(12) United States Patent
Govari et al.

(10) Patent No.: US 9,962,217 B2
(45) Date of Patent: May 8, 2018

(54) ESTIMATION AND MAPPING OF ABLATION VOLUME

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yaron Ephrath, Karkur (IL)

(73) Assignee: Biosense Webster (Israel) Ltd. (IL)

( * ) Notice: Subject to any disclaimer, the term of this patent is extended or adjusted under 35 U.S.C. 154(b) by 460 days.

(21) Appl. No.: 14/548,991

(22) Filed: Nov. 20, 2014

(65) Prior Publication Data

US 2016/0143696 A1    May 26, 2016
US 2017/0319258 A9    Nov. 9, 2017

Related U.S. Application Data

(62) Division of application No. 12/646,197, filed on Dec. 23, 2009, now Pat. No. 8,926,604.

(51) Int. Cl.
*A61B 18/14* (2006.01)
*A61B 18/12* (2006.01)
(Continued)

(52) U.S. Cl.
CPC .......... *A61B 18/12* (2013.01); *A61B 18/1206* (2013.01); *A61B 34/10* (2016.02);
(Continued)

(58) Field of Classification Search
CPC ............ A61B 18/1206; A61B 18/1492; A61B 2018/00738; A61B 2018/00761; A61B 2018/00779; A61B 2018/1465; A61B 2018/00636; A61B 2018/00351; A61B 2018/00357; A61B 2018/00577; A61B 2018/00791; A61B 2018/00642; A61B 2018/0066; A61B 2018/00648; A61B 2018/00702; A61B 2018/00714; A61B 2090/065
(Continued)

(56) References Cited

U.S. PATENT DOCUMENTS 5,396,887 A    3/1995  Imran
6,226,542 B1   5/2001  Reisfeld
(Continued)

OTHER PUBLICATIONS

Canadian Examination Report dated Oct. 28, 2016 from corresponding Canadian Patent Application No. 2,725,865.
(Continued)

*Primary Examiner* — Thomas Giuliani
(74) *Attorney, Agent, or Firm* — Vincent J. Serrao

(57) ABSTRACT

Tissue ablation systems and methods are provided, wherein a cardiac catheter incorporates a pressure detector for sensing a mechanical force against the distal tip when engaging an ablation site. Responsively to the pressure detector, a controller computes an ablation volume according to relationships between the contact pressure against the site, the power output of an ablator, and the energy application time. A monitor displays a map of the heart which includes a visual indication of the computed ablation volume. The monitor may dynamically display the progress of the ablation by varying the visual indication.

7 Claims, 5 Drawing Sheets

(51) Int. Cl.
*A61B 34/10* (2016.01)
*A61B 18/00* (2006.01)
*A61B 90/00* (2016.01)

(52) U.S. Cl.
CPC ... *A61B 18/1492* (2013.01); *A61B 2018/0066* (2013.01); *A61B 2018/00184* (2013.01); *A61B 2018/00351* (2013.01); *A61B 2018/00577* (2013.01); *A61B 2018/00642* (2013.01); *A61B 2018/00702* (2013.01); *A61B 2018/00761* (2013.01); *A61B 2018/00791* (2013.01); *A61B 2018/1465* (2013.01); *A61B 2090/065* (2016.02)

(58) Field of Classification Search
USPC .......... 606/34, 38, 41, 42; 607/99, 101, 102, 607/105, 113, 116, 119, 122
See application file for complete search history.

(56) References Cited

U.S. PATENT DOCUMENTS

| | | |
|---|---|---|
| 6,241,724 B1 | 6/2001 | Fleischman et al. |
| 6,272,371 B1 | 8/2001 | Shlomo |
| 6,301,496 B1 | 10/2001 | Reisfeld |
| 6,332,089 B1 | 12/2001 | Acker et al. |
| 6,618,612 B1 | 9/2003 | Acker et al. |
| 6,690,963 B2 | 2/2004 | Ben-Haim et al. |
| 6,695,808 B2 | 2/2004 | Tom |
| 6,814,733 B2 | 11/2004 | Schwartz et al. |
| 6,892,091 B1 | 5/2005 | Ben-Haim et al. |
| 6,915,149 B2 | 7/2005 | Ben-Haim |
| 6,997,924 B2 | 2/2006 | Schwartz et al. |
| 7,001,383 B2 | 2/2006 | Keidar |
| 7,156,816 B2 | 1/2007 | Schwartz et al. |
| 7,306,593 B2 | 12/2007 | Keidar et al. |
| 8,097,926 B2 * | 1/2012 | De Graff ............ A61B 1/05 257/419 |
| 2002/0123749 A1 | 9/2002 | Jain |
| 2004/0068178 A1 | 4/2004 | Govari |
| 2004/0102769 A1 | 5/2004 | Schwartz et al. |
| 2004/0147920 A1* | 7/2004 | Keidar .................. A61B 5/06 606/34 |
| 2006/0287648 A1 | 12/2006 | Schwartz |
| 2007/0060832 A1 | 3/2007 | Levin |
| 2007/0100332 A1 | 5/2007 | Paul et al. |
| 2007/0191830 A1* | 8/2007 | Crompton ............ A61B 18/14 606/41 |
| 2008/0161796 A1* | 7/2008 | Cao .................. A61B 18/1492 606/41 |
| 2009/0076476 A1 | 3/2009 | Barbagli et al. |
| 2009/0093806 A1 | 4/2009 | Govari et al. |
| 2009/0138007 A1 | 5/2009 | Govari et al. |
| 2009/0306650 A1 | 12/2009 | Govari et al. |
| 2010/0160770 A1 | 6/2010 | Govari et al. |
| 2011/0130648 A1 | 6/2011 | Beeckler et al. |
| 2011/0152856 A1* | 6/2011 | Govari ............... A61B 18/1492 606/34 |
| 2014/0100563 A1* | 4/2014 | Govari ............... A61B 18/1492 606/41 |

OTHER PUBLICATIONS

Yokoyama, Katsuaki, M.D. et al., "Novel Contact Force Sensor Incorporated in Irrigated Radiofrequency Ablation Catheter Predicts Lesion Size and Incidence of Steam Pop and Thrombus", Circulation, Arrythmia and Electrophysiology, Jan. 1, 2008, pp. 354-362, vol. 1.

Poster Session 1: P001 to P001-70, Heart Rhythm, Elsevier, US, vol. 6. No. 5. May 1, 2009 pp. S95-S120 ISSN 1547-5271.

European Search Report dated May 9, 2011 from corresponding European Application No. 10252190.3.

Australian Exam Report dated Jun. 13, 2014 from corresponding Australian Application No. 2010257204.

* cited by examiner

ESTIMATION AND MAPPING OF ABLATION VOLUME

This application is a divisional application of U.S. patent application Ser. No. 12/646,197, filed on Dec. 23, 2009, now U.S. Pat. No. 8,926,604, the entire contents of which are hereby incorporated by reference herein.

BACKGROUND OF THE INVENTION

Field of the Invention

This invention relates to relates generally to minimally invasive treatment of organs inside the body. More particularly, this invention relates to methods and devices for prediction and assessment of ablation treatments applied to cardiac tissue.

Description of the Related Art

Intracardiac radio-frequency (RF) ablation is a well known method for treating cardiac arrhythmias. Typically, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. It is important to ensure proper contact between the electrode and the endocardium during ablation in order to achieve the desired therapeutic effect without excessive damage to the tissue.

Various techniques have been suggested for verifying electrode contact with the tissue. For example, U.S. Pat. No. 6,695,808, whose disclosure is incorporated herein by reference, describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724, whose disclosure is incorporated herein by reference, describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149, whose disclosure is incorporated herein by reference. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332, whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

Visualization of ablation lesions in real time is important in enabling the physician to ensure that each point along the treatment path has been sufficiently ablated to interrupt conduction, while avoiding the dangers of excessive ablation. U.S. Pat. No. 7,306,593, issued to Keidar et al., whose disclosure is herein incorporated by reference, describes a method for ablating tissue in an organ by contacting a probe inside the body with the tissue to be ablated, and measuring one or more local parameters at the position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

SUMMARY OF THE INVENTION

It has been found experimentally that the volume of heart tissue ablated when RF energy is applied by a catheter electrode in contact with the tissue at a given point is roughly proportional to the RF power (P) and roughly proportional to the mechanical force (F) between the catheter and the tissue. Thus, the P*F product gives a good indication of the rate of ablation of the tissue and may be used in real-time mapping of the volume of tissue ablated.

An embodiment of the invention provides a method of ablation, which is carried out by inserting a probe into a body of a living subject, urging the probe into contact with a tissue in the body, determining a mechanical force that is exerted by the probe against the tissue, and applying a specified dosage of energy to the tissue for ablation thereof, wherein at least one of the application time of the dosage and the power level depend on the mechanical force.

An aspect of the method is performed prior to applying the specified dosage of energy by reporting an indication of an expected ablation volume at the power level, the application time and the mechanical force.

A further aspect of the method includes displaying a visual indication of the ablation volume, and responsively to the visual indication controlling the ablation volume by varying at least one of the power level, the mechanical force and the application time.

Another aspect of the method includes calculating a rate of ablation as a function of the power level and the mechanical force, and controlling the rate of ablation by varying at least one of the power level and the mechanical force.

Still another aspect of the method includes monitoring tissue temperature of the tissue and controlling the rate of ablation is performed responsively to the temperature.

Other embodiments of the invention provide apparatus for carrying out the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Figure 1:
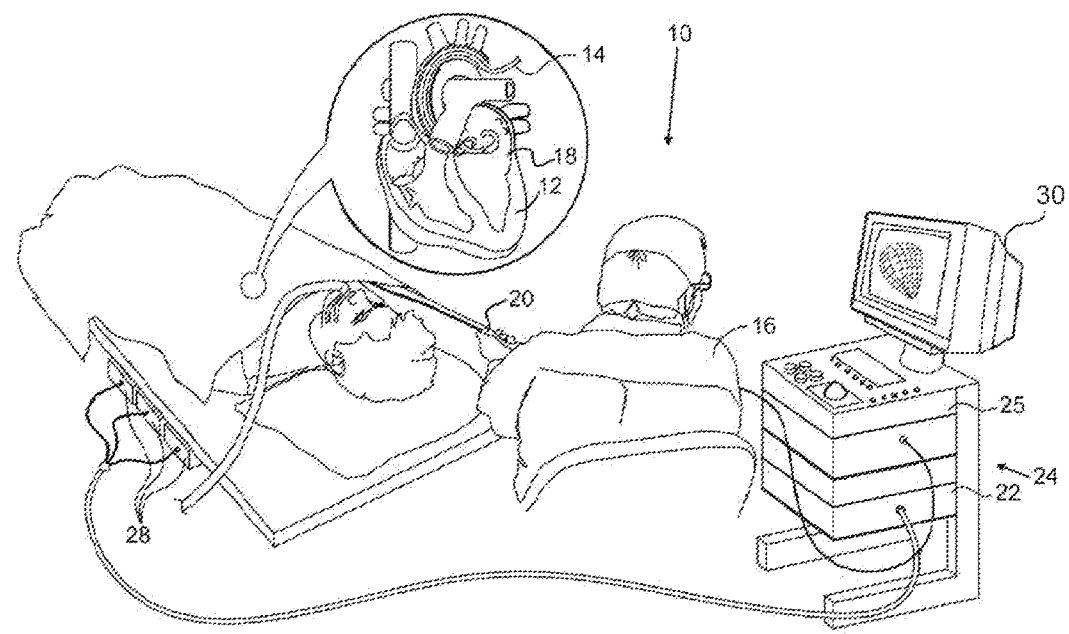
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart. The operator 16, who is typically a physician, brings the catheter's distal tip 18 into contact with the heart wall at an ablation target site. Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. Although the embodiment described with respect to FIG. 1 is concerned primarily with cardiac ablation, the principles of the invention may be applied, mutatis mutandis, to other catheters and probes and to body tissues other than the heart.

Areas determined to be abnormal by evaluation of the electrical activation maps can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/0102769, whose disclosure is herein incorporated by reference. The principles of the invention can be applied to different heart chambers, and to mapping in sinus rhythm, and when many different cardiac arrhythmias are present.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24. The console 24 typically contains an ablation power generator 25. The catheter 14 may be adapted to conduct ablative energy to the heart using any known ablation technique, e.g., radiofrequency energy, ultrasound energy, and laser energy. Such methods are disclosed in commonly assigned U.S. Pat. Nos. 6,814,733, 6,997,924, and 7,156,816, which are herein incorporated by reference.

The positioning processor 22 is an element of a positioning sub-system of the system 10 that measures location and orientation coordinates of the catheter 14.

In one embodiment, the positioning sub-system comprises a magnetic position tracking arrangement that determines the position and orientation of the catheter 14 by generating magnetic fields in a predefined working volume its vicinity and sensing these fields at the catheter. The magnetic position tracking arrangement typically comprises a set of external radiators, such as field generating coils 28, which are located in fixed, known positions external to the patient. The field generating coils 28 are driven by field generators (not shown), which are typically located in the console 24, and generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking techniques that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning sub-system shown in FIG. 1 uses magnetic fields, the methods described below may be implemented using any other suitable positioning system, such as systems based on electromagnetic fields, acoustic or ultrasonic measurements. A suitable commercial positioning sub-system is the CARTO XP EP Navigation and Ablation System, available from Biosense Webster, Inc., 3333 Diamond Canyon Road, Diamond Bar, Calif. 91765.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 30. The signal processing circuits typically receive, amplify, filter and digitize signals from the catheter 14, including signals generated by the above-noted sensors and a plurality of sensing electrodes (not shown) located distally in the catheter 14. The digitized signals are received and used by the console 24 to compute the position and orientation of the catheter 14 and to analyze the electrical signals from the electrodes. The information derived from this analysis may be used to generate an electrophysiological map of at least a portion of the heart 12 or structures such as the pulmonary venous ostia, for diagnostic purposes such as locating an arrhythmogenic area in the heart or to facilitate therapeutic ablation.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. By comparing the position of the catheter 14 to that of the reference catheter, the coordinates of catheter 14 are determined relative to the heart 12, irrespective of heart motion. Alternatively, any other suitable method may be used to compensate for heart motion. Nevertheless, the positioning sub-system cannot guarantee that an energy-conveying component of the catheter 14 is in actual contact with the tissue to be ablated.

Figure 2:
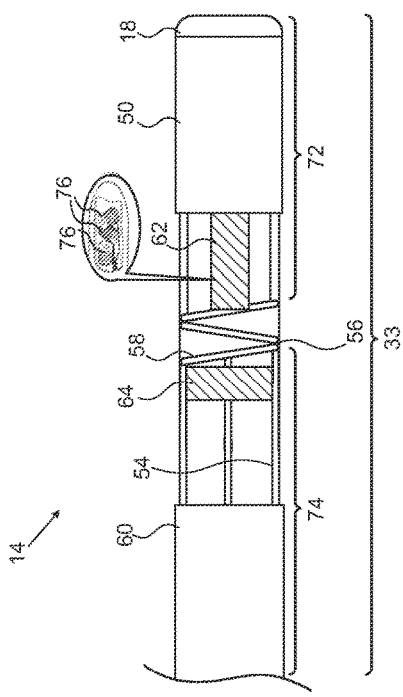
FIG. 2 is a cutaway view of the distal end of a catheter used in the system shown in FIG. 1, in accordance with an embodiment of the present invention.

Reference is now made to FIG. 2, which is a cutaway view of distal end 33 of catheter 14 (FIG. 1), showing details of the structure of the catheter in accordance with an embodiment of the present invention. The catheter shown in FIG. 2 includes a pressure transducer, which is more fully disclosed in commonly assigned U.S. Patent Application Publication No. 2009/0093806, which is herein incorporated by reference. Other known types of pressure transducers can be substituted for the pressure transducer described with reference to FIG. 2.

Catheter 14 comprises a flexible insertion tube 54, with a distal section 72 connected to the remainder of the insertion tube 54 at a joint 56. The insertion tube is covered by a flexible, insulating material 60, such as Celcon™ or Teflon™. The area of joint 56 is covered, as well, by a flexible, insulating material, which may be the same as material 60 or may be specially adapted to permit unimpeded bending and compression of the joint, (This material is cut away in FIG. 2 in order to expose the internal structure of the catheter.) Distal tip 18 may be covered, at least in part, by an electrode 50, which is typically made of a metallic material, such as a platinum/iridium alloy. Alternatively, other suitable materials may be used, as will be apparent to those skilled in the art. The distal section 72 is typically relatively rigid, by comparison with a proximal section 74.

The distal section 72 is connected to the proximal section 74 by a resilient member 58. In FIG. 2, the resilient member 58 has the form of a coil spring, but other types of resilient components may alternatively be used for this purpose. For example, resilient member 58 may comprise a polymer, such as silicone, polyurethane, or other plastics, with the desired flexibility and strength characteristics. Resilient member 58 permits a limited range of relative movement between distal section 72 and the proximal section 74 in response to forces exerted on the distal section 72 or directly against the distal tip 18. Such forces are encountered when the distal tip is pressed against the endocardium during an ablation procedure. The desired pressure for good electrical contact between the distal tip and the endocardium during ablation is on the order of 20-30 grams. The spring serving as the resilient member 58 in this embodiment may be configured, for example, to permit axial displacement (i.e., lateral movement along the axis of catheter 14) of the distal end 33 by about 1-2 mm and angular deflection of the distal section 72 with respect to the proximal section 74 by up to about 30 degrees in response to a desired pressure.

As noted above, distal section 72 contains a magnetic position sensor 62. Position sensor 62 may comprise one or more miniature coils, and typically comprises multiple coils oriented along different axes. Alternatively, position sensor 62 may comprise another type of magnetic sensor, such as a Hall effect or magnetoresistive sensor, for example. The magnetic fields created by the field generating coils 28 (FIG. 1) cause the position sensor 62 to generate electrical signals, with amplitudes that are indicative of the position and orientation of position sensor 62 relative to the fixed frame of reference of field generating coils 28. Positioning processor 22 (FIG. 1) receives these signals via wires (not shown in the figures) running through catheter 14, and processes the signals in order to derive the location and orientation coordinates of distal tip 18 in this fixed frame of reference, as described in the patents and patent applications cited above. Some of the position sensing and mapping features of the catheter 14 are implemented in the NOGA-STAR catheter and the and CARTO™ systems, marketed by Biosense Webster, Inc.

In addition, catheter 14 contains a miniature magnetic field generator 64 near the distal tip 18, which is driven by a current conveyed through catheter 14 from console 24 (FIG. 1). The current is generated so as to create magnetic fields that are distinguishable in time and/or frequency from the fields of field generating coils 28 (FIG. 1). For example, the current supplied to field generator 64 may be generated at a selected frequency in the range between about 16 kHz and 25 kHz, while field generating coils 28 are driven at different frequencies. Additionally or alternatively, the operation of field generating coils 28 and field generator 64 may be time-multiplexed.

The magnetic field created by field generator 64 causes one or more coils in position sensor 62 to generate electrical signals at the drive frequency of field generator 64. The amplitudes of these signals vary depending upon the location and orientation of distal tip 18 relative to proximal section 74. Positioning processor 22 (FIG. 1) processes these signals in order to determine the axial displacement and the magnitude of the angular deflection of the distal tip 18 relative to the proximal section 74. Position sensor 62 may determine six position and orientation coordinates (X, Y, Z directions and pitch, yaw and roll orientations) of the distal end and distal tip of catheter 14. For this purpose, at least two sensing coils are typically required in the position sensor. In the present embodiment, three sensing coils 76 are used, in order to improve the accuracy and reliability of the position measurement. Alternatively, if only a single sensing coil is used, system 10 may be able to determine only five position and orientation coordinates (X, Y, Z directions and pitch and yaw orientations). As the readings of displacement and deflection should be accurate to within a few tenths of a millimeter and about one degree, respectively, it is desirable to include three coils 76 in position sensor 62, preferably mutually orthogonal, as shown in FIG. 2.

As the position of the position sensor 62 with reference to some fixed frame of reference (not shown) can be determined, it is possible to compute the relative movement of the distal tip 18 relative to the proximal section 74. This gives a measure of the deformation and angular deviation of resilient member 58. Generally speaking, the deformation is proportional to the mechanical force that is exerted on the resilient member 58, which is roughly equal to the force that is exerted on the distal tip 18 by the heart tissue with which the distal tip 18 is in contact. Thus, the combination of field generator 64 with position sensor 62 serves as a pressure sensing system for determining the approximate pressure exerted by the endocardial tissue on the distal tip 18 of the catheter 14 (or equivalently, the pressure exerted by electrode 50 against the endocardial tissue).

Figure 3:
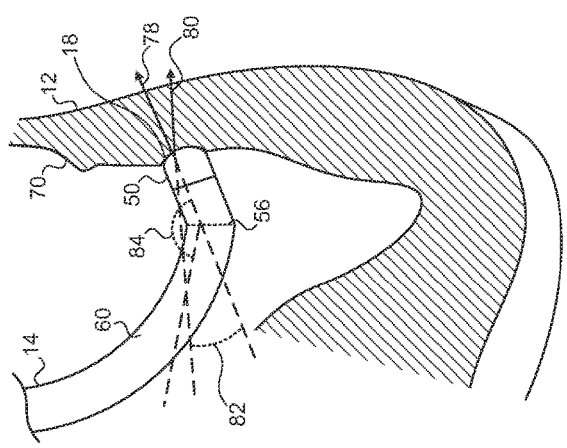
FIG. 3 is a pictorial view of the distal end of the catheter shown in FIG. 2 in contact with endocardial tissue, in accordance with an embodiment of the invention.

Reference is now made to FIG. 3, which is a pictorial view of the distal end 33 of the catheter 14 in contact with endocardium 70 of the heart 12, in accordance with an embodiment of the invention. Pressure exerted by the distal tip 18 against the endocardium 70 deforms the endocardial tissue slightly, so that the electrode 50 contacts the tissue over a relatively large area. Since the electrode 50 engages the endocardium 70 at an angle 82, rather than head-on, distal section 72 bends at joint 56 forming a bend angle 84 relative to the insertion tube of the catheter. The bend facilitates optimal contact between the electrode and the endocardial tissue.

Reverting to FIG. 2, positioning processor 22 (FIG. 1) receives and processes the signals generated by position sensor 62 in response to the magnetic field of generator 64, in order to derive an indication of the pressure exerted by distal tip 18 on endocardium 70 (FIG. 3). As noted earlier, for good ablation, pressure of about 20-30 grams is desirable. Lower pressure means that there may be inadequate contact between electrode 50 and the endocardial tissue. As a result, much or all of the thermal energy may be carried away by the blood inside the heart, and the tissue will be ablated inadequately or not at all. Higher pressure means that the electrode is pressing too hard against the endocardial tissue. Excessive pressure of this sort may cause cavitation in the tissue, leading to extensive tissue damage and possibly even perforation of the heart wall.

It is possible to determine the coordinates of the position sensor 62 with respect to some fixed frame of reference. In embodiments in which the field generator 64 has at least two coils it is also possible to determine the directional orientations of the axes of the position sensor 62 with respect to one another, and thereby compute the bend angle 84 (FIG. 3).

By virtue of the combined sensing of displacement and deflection, this pressure sensing system reads the pressure correctly regardless of whether the electrode engages the endocardium head-on or at an angle. The pressure reading is insensitive to temperature variations and free of drift, unlike piezoelectric sensors, for example.

The magnitudes of the displacement and deflection may be combined by vector addition to give a total magnitude of the movement of distal tip 18 relative to the proximal section 74. When there are three coils, the system can determine the position of the distal section 72 and the distal tip 18 with six degrees of freedom. Force vectors 78, 80 can then be computed, the vector 80 representing the magnitude of the component that is normal to the wall of the heart 12. The relationships between force and deflection may be pre-calibrated for each catheter and a calibration table constructed and used subsequently in force measurements.

Referring again to FIG. 1, console 24 outputs an indication of the pressure measured to the operator 16, and may issue an alarm if the pressure is too low or too high. Optionally, ablation power generator 25 may be interlocked, so as to supply power to electrode 50 (FIG. 2) only when the pressure against the endocardium 70 (FIG. 3) is in the desired range. Alternatively or additionally, the pressure indication may be used in closed-loop control of an automated mechanism for maneuvering and operating catheter 14, as described more fully in the above noted U.S. Patent Application Publication No. 2004/0102769, in order to ensure that the mechanism causes the distal section 72 to engage the endocardium 70 (FIG. 3) in the proper location and with the appropriate contact pressure.

While RF power is discussed with respect to the methods and systems herein, in embodiments of the system 10 (FIG. 1), other forms of energy may be delivered to the tissue, i.e., laser and microwave techniques, and high intensity focused ultrasound energy, as described in commonly assigned U.S. Patent Application Publication No. 2006/0287648, which is herein incorporated by reference.

The product P*F gives a good indication of the rate of ablation of the tissue, where P represents RF power and F represents the magnitude of the force vector exerted by the catheter against the endocardial surface of the heart. The operator may increase or decrease either or both of the component parameters, P and F in order to control the ablation rate. The total volume V of tissue ablated, up to a maximum dictated by tissue characteristics and safety considerations, is roughly proportional to the product $$V \approx k(P*F*T) \tag{1},$$

wherein T is the time duration of RF power application, and k is a proportionality constant.

Figure 4:
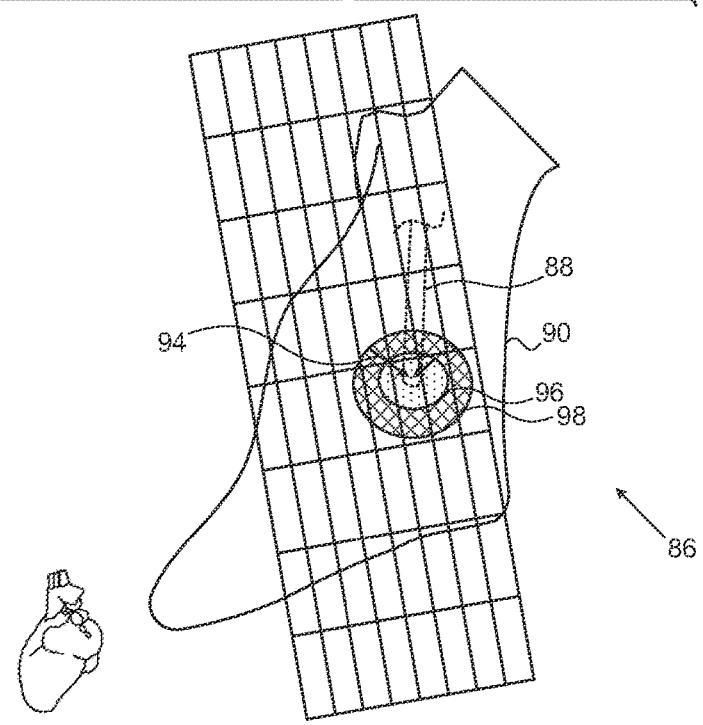
FIG. 4 is a composite map of the heart, illustrating aspects of a cardiac ablation procedure in accordance with an embodiment of the invention.

Reference is now made to FIG. 4, which is a composite map 86 of the heart illustrating aspects of a cardiac ablation procedure in accordance with a disclosed embodiment of the invention. The procedure may be actual or simulated, for purposes of predicting the necessary force to be applied by a cardiac catheter 88 in an operating position within a chamber of heart 90. Arrows 92, 94 represent two different force vectors, the length of the arrows corresponding to the magnitudes of the forces being. A dosage of energy, e.g., RF ablation current is to be applied at a predetermined power level for a time sufficient to produce an ablation lesion. Predicted small and large circular ablation zones 96, 98 correspond to the short and long arrows 92, 94, respectively.

Additionally or alternatively, when the force being applied and the RF power are known, the size of the ablation zone can be predicted and dynamically displayed. The completeness of the ablation can be calculated as time varies, and progress displayed during the procedure as by changing the visual characteristics of the ablation zones 96, 98. The ablation volume grows over time in proportion to the product P*F.

Similarly, by fixing the desired size of the ablation zone, the required force can be computed at a given RF power and application time or for a given total energy dosage at different combinations of application time and RF power.

Using the map 86, a simple, clear measure of estimated ablation volume is provided to the operator, which can be measured easily and accurately in near real-time.

Figure 5:
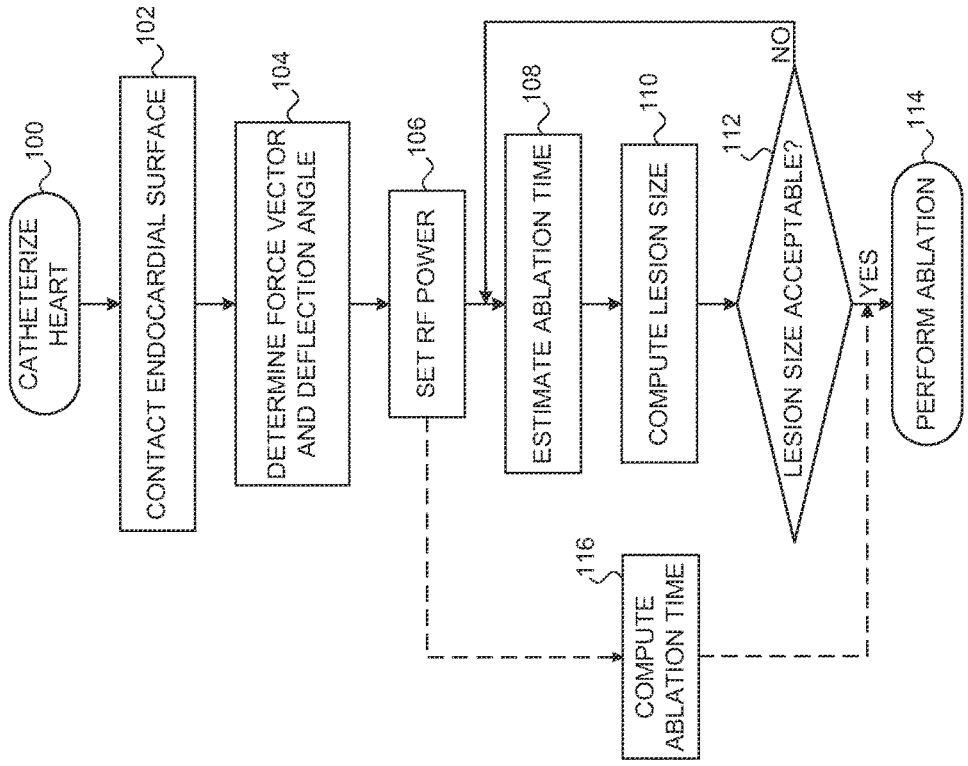
FIG. 5 is a flow chart of a method of estimation and mapping tissue ablation volume, in accordance with a disclosed embodiment of the invention.

Reference is now made to FIG. 5, which is a flow chart of a method of estimation and mapping of tissue ablation volume, in accordance with a disclosed embodiment of the invention. The method requires a determination of mechanical force developed by contact between a probe and the tissue site to be ablated. The method can be performed by the system 10 (FIG. 1) using catheter 14. However, other methods that are capable of measuring the pressure can be applied, for example impedance-based measurements, such as disclosed in commonly assigned U.S. Patent Application Publication No. 2007/0060832, whose disclosure is herein incorporated by reference. Alternatively, suitable optical or ultrasound techniques may be used to determine the mechanical force.

The process begins at initial step 100. The heart is catheterized conventionally and the catheter navigated to a desired location at which tissue ablation is required.

Next, at step 102, the cardiac catheter is brought into contact with the endocardial surface, generally at an angle of incidence other than perpendicular as shown in FIG. 3.

Next, at step 104, The mechanical force or a desired force vector applied to the endocardium by the catheter is determined. The deflection angle, e.g., angle 82 (FIG. 3) may be determined automatically, using the information provided by location sensors in the catheter.

Next, at step 106, ablation power, e.g., RF power, is determined for the current medical procedure.

Then, at step 108, an estimated ablation time is tentatively chosen, which establishes the energy dosage to be applied. Alternatively, steps 106, 108 can be modified to set the ablation time, and estimate power levels, respectively. The operator may be assisted at this step in that a controller may report an indication of an expected ablation volume at the energy dosage and the mechanical force.

Next, at step 110 the size of the lesion to be created by ablating is computed, according to the conditions established in step 104 and step 108.

Control now proceeds to decision step 112, where it is determined if the current lesion size is acceptable. If the determination at decision step 112 is affirmative, then control proceeds to final step 114, where power, typically RF power, is applied, and ablation is performed. During the ablation the currently ablated tissue volume is dynamically displayed as shown in FIG. 4 until the computed ablation volume has been achieved. The operator may vary the power to control the time of application. Additionally or alternatively the operator may adjust the position of the catheter to vary the mechanical force applied to the endocardial tissues.

If the determination at decision step 112 is negative, then control returns to step 108, where the ablation time is re-estimated.

Typically, the size of the lesion to be created by ablation is known. In such cases, the loop defined by step 108, step 110 and decision step 112 can be iterated automatically until an acceptable size has been determined.

Alternatively the lesion size may be computed directly at optional step 116 using the relationship of Equation 1, and then perform ablation at final step 114. In this case, step 108, step 110 and decision step 112 can be omitted.

In alternate embodiments of the method, proposed power and proposed application time data can be received as input and ablation volumes computed at different mechanical forces of contact with the tissue.

ALTERNATE EMBODIMENT

Figure 6:
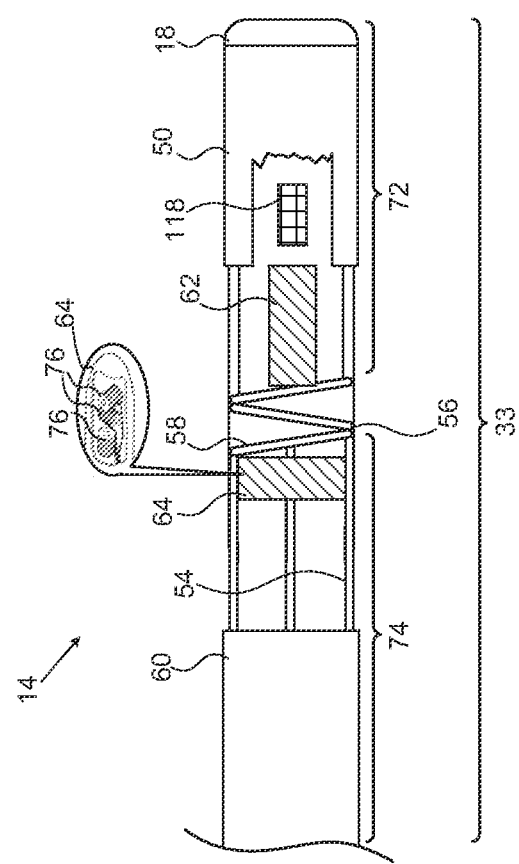
FIG. 6 is a cutaway view of a catheter used in the system shown in FIG. 1, which is constructed and operative in accordance with an alternate embodiment of the invention.

Reference is now made to FIG. 6, which is a cutaway view of distal end 33 of catheter 14 (FIG. 1), which is constructed and operative in accordance with a disclosed embodiment of the invention. This embodiment is similar to FIG. 2, except now the distal section 72 includes a conventional temperature sensor 118 that is capable of detecting abnormal rise in temperature of the tissues at the operating site. By displaying the output of the temperature sensor 118 on the monitor 30 (FIG. 1) or providing a suitable audible alert, the rate of ablation may be controlled by responsively to the temperature of the tissues in order to prevent charring or dangerous temperature elevation outside the computed ablation volume.

Equation 1 can be modified to account for the temperature such that only actual ablation time, rather than total elapsed time is taken into consideration. Ablation time can be defined to run only when contact force exceeding a predetermined force threshold is ascertained and the temperature exceeds a predetermined temperature threshold. Alternatively, ablation time can be defined to run only when contact force exceeding a predetermined force threshold is ascertained or the temperature exceeds a predetermined temperature threshold.

Equation 1 may be modified in several ways to account for ablation time. The following examples are practical approximations, in which various first and second order corrections are not shown for clarity of presentation. The threshold values given below are suitable:

$$V \approx k*(P*F*T(F>F_{threshold})) \qquad (2)$$

$$V \approx k*(P*F*T(F>F_{threshold}, t>t_{threshold})) \qquad (3)$$

$$V \approx k*(P*F*T(t>t_{threshold}) \qquad (4)$$

wherein $F_{threshold}=5$ gr, and $t_{threshold}=47°$ C. The ablation power is applied only during time intervals when the conditions shown are met.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

What is claimed is:

1. A method of ablation, comprising the steps of: inserting a probe into a body of a living subject; urging the probe into contact with a tissue in the body; determining a mechanical force that is exerted by the probe against the tissue; calculating a rate of ablation as a function of a power level and the mechanical force; applying a specified dosage of energy for an application time and at the power level to the tissue for ablation thereof, wherein at least one of the application time of the dosage and the power level depend on the mechanical force; and controlling the rate of ablation by varying at least one of the power level and the mechanical force.

2. The method according to claim 1, further comprising the step of prior to applying the specified dosage of energy, reporting an indication of an expected ablation volume at the power level, the application time and the mechanical force.

3. The method according to claim 1, wherein the probe has a distal end and an axis, and urging the probe comprises forming an angular deflection of the distal end with respect to the axis.

4. The method according to claim 1, further comprising the steps of calculating an ablation volume of the tissue as a function of the power level, the mechanical force and the application time.

5. The method according to claim 4, further comprising the steps of:
   displaying a visual indication of the ablation volume; and
   responsively to the visual indication controlling the ablation volume by varying at least one of the power level, the mechanical force and the application time.

6. The method according to claim 1, further comprising displaying a visual indication of the rate of ablation, wherein controlling the rate of ablation is performed responsively to the visual indication.

7. The method according to claim 1, further comprising monitoring a temperature of the tissue, wherein controlling the rate of ablation is performed responsively to the temperature.

* * * * *